US009480481B2

(12) United States Patent
McEwen et al.

(10) Patent No.: US 9,480,481 B2
(45) Date of Patent: *Nov. 1, 2016

(54) LOW COST TOURNIQUET CUFF WITH INTEGRATED MANUFACTURE INDICIA

(71) Applicant: Western Clinical Engineering Ltd., Vancouver (CA)

(72) Inventors: James A. McEwen, Vancouver (CA); Michael Jameson, North Vancouver (CA); Kenneth L. Glinz, Richmond (CA); Allen J. Upward, Vancouver (CA)

(73) Assignee: Western Clinical Engineering Ltd., Vancouver (CA)

( * ) Notice: Subject to any disclaimer, the term of this patent is extended or adjusted under 35 U.S.C. 154(b) by 853 days.

This patent is subject to a terminal disclaimer.

(21) Appl. No.: 13/864,160

(22) Filed: Apr. 16, 2013

(65) Prior Publication Data
US 2013/0245673 A1 Sep. 19, 2013

Related U.S. Application Data

(63) Continuation of application No. 13/424,067, filed on Mar. 19, 2012, now Pat. No. 8,425,551, which is a continuation of application No. 12/497,515, filed on Jul. 2, 2009, now Pat. No. 8,142,472, which is a continuation of application No. 11/346,846, filed on Feb. 3, 2006, now abandoned, which is a continuation-in-part of application No. 11/304,363, filed on Dec. 14, 2005, now Pat. No. 8,137,378.

(51) Int. Cl.
*A61B 17/00* (2006.01)
*A61B 17/135* (2006.01)
*A61B 17/132* (2006.01)

(52) U.S. Cl.
CPC ......... *A61B 17/135* (2013.01); *A61B 17/1322* (2013.01); *A61B 2017/0023* (2013.01); *Y10T 156/10* (2015.01)

(58) Field of Classification Search
CPC ............ A61B 17/132; A61B 17/1322; A61B 17/1325; A61B 17/135; A61B 2017/00955; A61B 2017/0023; A61B 2017/12004; A61B 5/02255; A61B 5/02233; A61B 5/022; A61F 2013/00463; A61F 2013/00468; A61F 5/34; A61H 9/0078
See application file for complete search history.

(56) References Cited

U.S. PATENT DOCUMENTS

| | | | | |
|---|---|---|---|---|
| 3,504,675 A | * | 4/1970 | Bishop, Jr. ......... | A61B 17/1322 606/202 |
| 3,670,735 A | * | 6/1972 | Hazlewood .......... | A61B 17/135 606/202 |
| 4,635,635 A | * | 1/1987 | Robinette-Lehman | A61B 17/135 606/202 |
| 4,770,175 A | * | 9/1988 | McEwen ............ | A61B 17/1355 600/492 |

(Continued)

*Primary Examiner* — Melanie Tyson
*Assistant Examiner* — Erin Colello
(74) *Attorney, Agent, or Firm* — Klarquist Sparkman, LLP

(57) ABSTRACT

A tourniquet cuff includes a first sheet, a second sheet, and a seal joining the first sheet and second sheet to form an inflatable bladder. A securing strap is attached to the cuff. The cuff encircles the limb so that the bladder overlaps upon itself. A stiffener fits inside the bladder and sized to extend substantially the length of the bladder but not the entire bladder length, and to fit completely within the seal. A tubular port is connected to the bladder for directing gas into the bladder from a tourniquet instrument to which the port may be releasably connected, and a cuff marking weld is located on an outer surface of the cuff, having a shape selected to form a symbol or indicia that is visible to a user.

3 Claims, 6 Drawing Sheets

(56) References Cited

U.S. PATENT DOCUMENTS

| | | | | |
|---|---|---|---|---|
| 4,979,953 A * | 12/1990 | Spence | ............... | A61B 17/135 600/499 |
| 5,411,518 A * | 5/1995 | Goldstein | ............ | A61B 17/135 600/499 |
| 5,733,304 A * | 3/1998 | Spence | ............... | A61B 17/135 606/203 |
| 6,682,547 B2 * | 1/2004 | McEwen | ............... | A61B 17/135 356/425 |
| 2006/0287672 A1 * | 12/2006 | McEwen | ............... | A61B 17/135 606/202 |

* cited by examiner

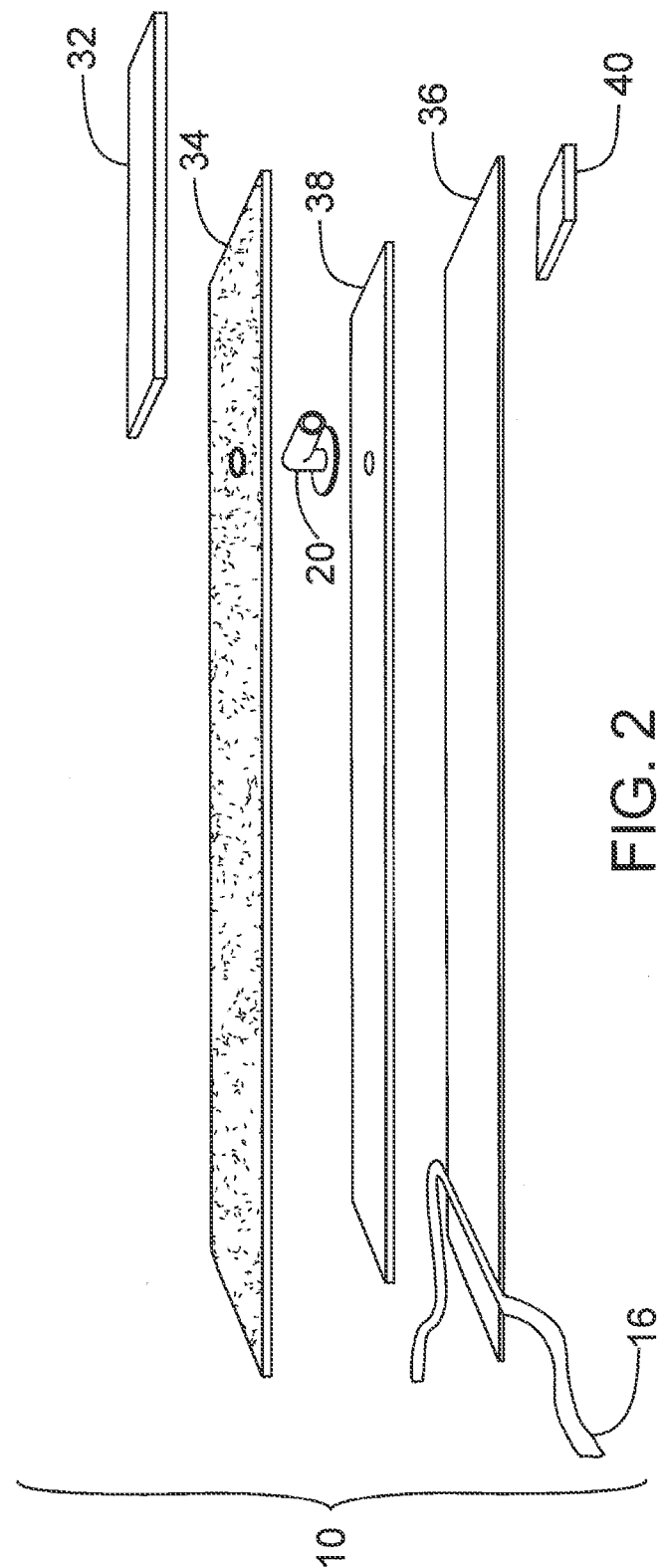

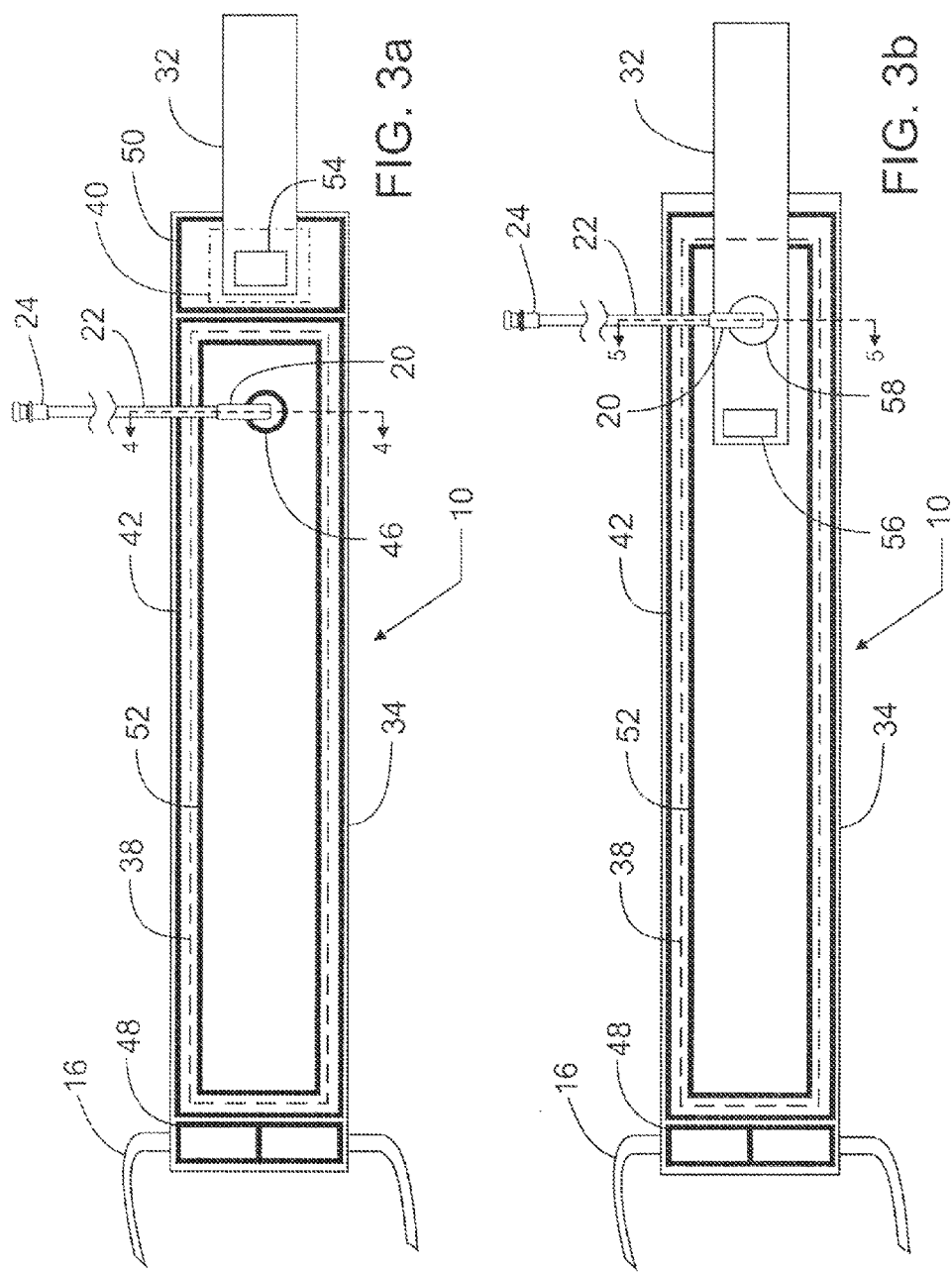

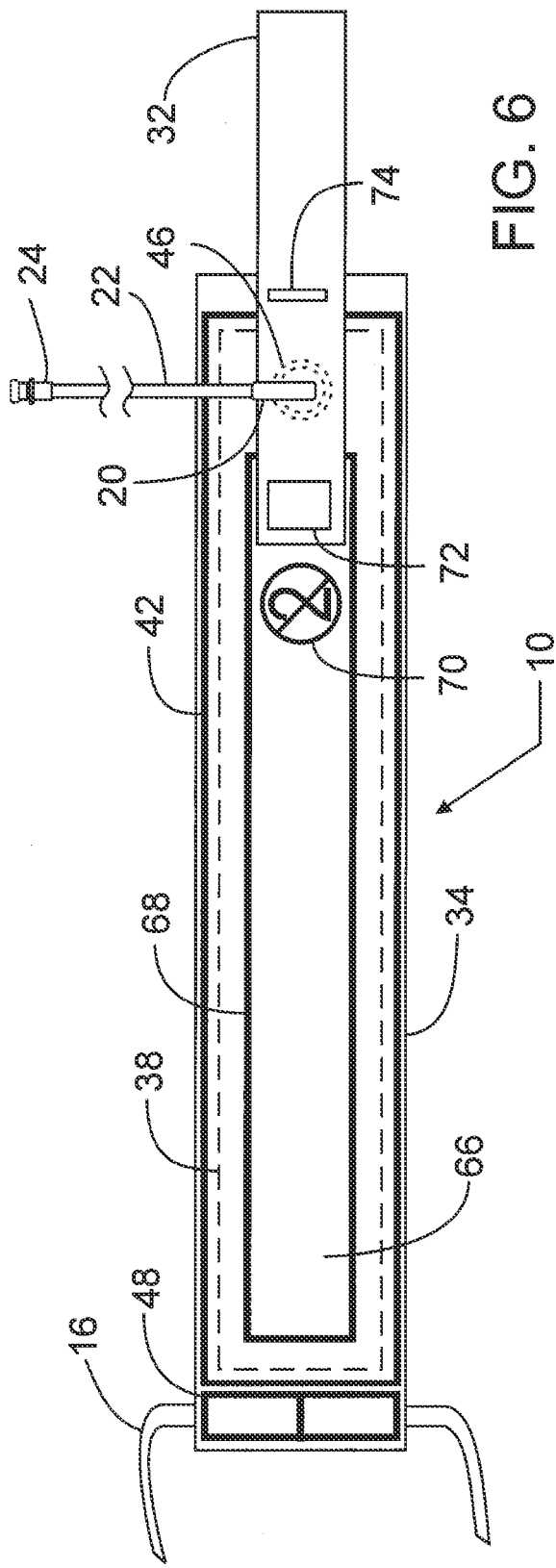

LOW COST TOURNIQUET CUFF WITH INTEGRATED MANUFACTURE INDICIA

This is a continuation of U.S. patent application Ser. No. 13/424,067, now U.S. Pat. No. 8,425,551 filed Apr. 23, 2013, which is a continuation of U.S. patent application Ser. No. 12/497,515, filed Jul. 2, 2009, now U.S. Pat. No. 8,142,472, which is a continuation of U.S. patent application Ser. No. 11/346,846, filed Feb. 3, 2006, now abandoned, which is a continuation-in-part of U.S. patent application Ser. No. 11/304,363, filed Dec. 14, 2005, now U.S. Pat. No. 8,137,378, all three of which applications are hereby incorporated by reference.

FIELD OF THE INVENTION

This invention pertains to pneumatic tourniquet cuffs commonly used for stopping arterial blood flow into a portion of a surgical patient's limb to facilitate the performance of a surgical procedure, and for facilitating intravenous regional anesthesia.

BACKGROUND OF THE INVENTION

Typical surgical tourniquet systems of the prior art include a tourniquet cuff which encircles the limb of a surgical patient and a tourniquet instrument which is releasably connected to an inflatable bladder within the tourniquet cuff through a length of tubing, thereby establishing a gas-tight passageway between the cuff and the tourniquet instrument. The tourniquet instrument contains a pressurized gas source which is used to inflate and regulate the pressure in the tourniquet cuff above a minimum pressure required to stop arterial blood flow distal to the cuff, for a duration suitably long for the performance of a surgical procedure. Many types of surgical tourniquet systems have been described in the prior art, such as those described by McEwen in U.S. Pat. No. 4,469,099, No. 4,479,494, No. 5,439,477 and McEwen and Jameson in U.S. Pat. No. 5,556,415 and No. 5,855,589.

A number of different types of disposable tourniquet cuffs are known in the prior art. These cuffs are intended to be used within sterile surgical fields, and are typically sterilized at the time of manufacture. Examples of multi-layer disposable cuffs in the prior art are described by Robinette-Lehman in U.S. Pat. No. 4,635,635, and in commercial products manufactured in accordance with its teachings ("Banana Cuff" sterile disposable tourniquet cuffs, Zimmer Arthroscopy Systems, Englewood Colo.), and by Guzman et al. in U.S. Pat. No. 6,506,206, and in commercial products manufactured according to its teachings ("Comfortor™ Disposable Gel Cuff", DePuy Orthopaedics Inc., Warsaw Ind.). A two-layer disposable cuff of the prior art is described by Spence in U.S. Pat. No. 5,733,304. Other disposable cuffs of the prior art have been constructed using multiple layers of costly materials such as cloth/thermoplastic laminates and gels. The use of multiple layers of such materials in prior-art cuffs has increased their overall thickness and stiffness, making these cuffs difficult for a surgical user to apply consistently. Thicker and stiffer cuffs of the prior art may also degrade performance after cuff application so that higher tourniquet pressures may be required to reliably occlude blood flow; this is undesirable because higher tourniquet pressures are associated in the surgical literature with a higher risk of patient injury.

Typical tourniquet cuffs of the prior art include a sealed inflatable bladder that encircles the limb and communicates pneumatically with a connected tourniquet instrument through one or more cuff ports, a stiffener that helps direct the expansion of the bladder radially inwards towards the limb and helps prevent any twisting or rolling of the cuff on the limb, and one or more fasteners that secure the cuff around the limb.

In order to facilitate the attachment of fasteners and cuff ports, the manufacture of prior art cuffs having multiple layers typically includes several labor-intensive operations, some of which require a high level of skill, quality and consistency on the part of manufacturing personnel. These operations can include sewing fastener materials to an outer cuff layer, adding a structural reinforcing patch to the outer layer, sealing one or more ports to a layer forming part of the inflatable bladder, and sealing layers around a perimeter to form the bladder.

Cuff layers consisting of compatible thermoplastic polymeric materials are typically joined together using a radio frequency (RF) welding process, which uses a combination of heat and pressure to cause compatible polymers to flow together by molecular diffusion. Welding operations to make cuffs of the prior art are typically completed in multiple steps, each of which typically requires the involvement of manufacturing personnel. For example, some cuffs have inflatable bladders formed from two separate sheets of thermoplastic coated material that are sealed around a perimeter using an RF welding process. Gas passageways into the bladder are typically formed using single or multiple ports welded to one layer before the bladder is formed. Each port provides a gas passageway into the bladder through a reinforced structure that is attached to tubing extending outside the sterile surgical field for connection to a tourniquet instrument. During the manufacturing process, the port is typically attached to one side of the bladder in a welding operation before the bladder is formed, to prevent the opposite bladder surface from being welded at the port location.

Many tourniquet cuffs of the prior art include a thermoplastic stiffener, which helps direct the expansion of the cuff bladder radially inward toward the limb when pressurized and helps reduce any tendency of the cuff to twist when pressurized or to roll distally down a tapered limb. The absence of a stiffener can lead to a reduction of the efficient application of pressure to the limb and thus can lead to an increase in the level of pressure required to stop blood flow past the cuff and into the limb. Also, the absence of a stiffener can lead to additional stresses in the outer cuff surface due to less constrained bladder expansion.

In many commonly used types of tourniquet cuffs of the prior art (such as Zimmer ATS sterile disposable tourniquet cuffs distributed by Zimmer Inc., Dover Ohio), a non-inflating sheath contains a stiffener outside an inflatable bladder. This configuration helps constrain the expansion of the bladder inwardly into the soft tissues of the limb encircled by the cuff when the cuff is pressurized, and helps prevent any twisting or rolling of the cuff on the limb. A second type of stiffener configuration involves increasing the thickness and rigidity of the material forming the outer cuff layer, to obtain a stiffening function from the outer layer in a two-layer cuff design (for example, as described by Eaton in U.S. Pat. No. 5,413,582, and in tourniquet cuffs distributed by Oak Medical, Briggs, North Lincs, UK). The outer layer of these prior-art tourniquet cuffs serves both as a stiffener and as one side of the inflatable bladder. The thick outer layer extends to all of the cuff edges, and includes an area for sealing the inner layer to the thick outer layer to form an inflatable bladder, resulting in the bladder always having a bladder width that is less than the width of the stiffener; this is undesirable because cuffs having narrower bladder widths require higher tourniquet pressures to stop blood flow, and higher tourniquet cuff pressures are associated with a higher risk of patient injury. Also, this second type of stiffener configuration in cuffs of the prior art, in which the stiffener forms part of the inflatable bladder, greatly limits the extent to which the cuff can expand inwardly into soft tissue when the cuff is pressurized; this limitation increases the pressure required to stop or occlude blood flow in the encircled limb, especially in obese patients and patients having large amounts of soft tissue. Further, the thick and stiff edges formed at the side edges of these prior-art cuffs may have a tendency to buckle towards the limb when the bladder is pressurized, leading to a potential soft-tissue hazard. A third stiffener configuration in tourniquet cuffs of the prior art includes an unsecured stiffener located within the inflatable bladder (for example, as described by Goldstein et al. in U.S. Pat. No. 5,411,518, by Spence in U.S. Pat. No. 5,733,304, and as seen in "Color Cuff II" sterile disposable tourniquet cuffs distributed by InstruMed Inc., Bothell Wash.). In this configuration, the stiffener is unsecured within the bladder and does not constrain the expansion of the outer cuff surface. This reduces the effectiveness of the stiffener in directing cuff pressure toward the encircled limb across the width of the cuff, and it reduces the extent to which the cuff can expand inwardly when pressurized, thereby making its performance more sensitive to variations in application technique and thereby leading to the possible need for higher tourniquet pressures to stop blood flow past the cuff and into the limb, particularly in patients having large amounts of soft tissue and in patients with poor muscle tone. Further, an unsecured stiffener within the cuff bladder is not as effective as a secured stiffener in helping to prevent the cuff from twisting or rolling on the limb. In addition, to reduce the limitations of performance that are inherent in a cuff having an unsecured stiffener within the inflatable bladder, the width of the stiffener in prior art cuffs must be as close as possible to the bladder width; this can impair cuff performance and requires precise alignment of the stiffener during manufacture.

Many cuffs of the prior art include velcro-type fastening elements, commonly referred to as hook and loop fasteners. The most common configuration consists of a hook-type fastening strap adapted for engaging with a loop-type material on the outer surface of the cuff to form a releasable velcro-type attachment when the cuff encircles a limb. In U.S. Pat. No. 5,201,758 Glover describes a multi-layer tourniquet cuff having a bladder contained within a flexible covering and a backing plate, and a fabric strap of loop-type material attached at one end to the outer side of the backing plate, for releasably engaging with a strip of hook-type material permanently mounted to the outer side of the backing plate. In U.S. Pat. No. 5,411,518 Goldstein et al. describe a two-layer tourniquet cuff having a hook or loop fastening strap for engaging with an outer cuff surface of loop or hook material. In U.S. Pat. No. 5,413,582 Eaton describes a tourniquet cuff having two sheets joined at the sides and ends to form an inflatable bladder, wherein a fabric strap of hook-type material is attached to the outer sheet of the cuff by welding or by an adhesive, and wherein one end of a loop-type fabric tongue is attached to the outer cuff sheet by welding or by an adhesive. Eaton '582 further describes a flange that passes through an opening in the fabric tongue to help reduce the potential for a user accidentally pulling the fabric tongue off the outer sheet while tightening the cuff about a patient's limb. In U.S. Pat. No. 5,733,304 Spence describes a tourniquet cuff having a bladder with inner and outer walls and a fastening strap with anchored and free portions, wherein the anchored portion is attached to the outer wall of the bladder with a velcro-type connection and wherein the free portion is adapted to be releasably anchored by a user to the outer wall with a velcro-type connection. Spence '304 includes a hole in the fastening strap to allow the cuff port to help permanently secure the fastening strap, as described previously in Eaton '582.

Some tourniquet cuffs of the prior art include secondary fastening elements to provide increased safety and to facilitate cuff application. In U.S. Pat. No. 5,312,431 McEwen describes a tourniquet cuff having a primary fastening means to secure the bladder and a secondary fastening means which is independent of the primary fastening means. McEwen '431 provides increased safety by ensuring the bladder remains overlapped and secured in a substantially circumferential direction by the secondary velcro-type fastening means even if the primary fastening means is not engaged or becomes ineffective while the cuff is inflated. The primary fastening means of McEwen '431 further facilitates cuff application and alignment of a cuff end by providing a velcro-type patch near the cuff end for releasable attachment of the end to a surface of the cuff. In U.S. Pat. No. 5,193,549 Bellin et al. describe a tourniquet cuff with a hook-type patch attached to a loop-type cuff surface near an end by welding, adhesive or sewing, wherein the patch facilitates releasable attachment of the cuff end to the surface to secure the cuff around a limb. The two-layer tourniquet cuff described in Spence '304 includes primary and secondary fastening means similar to McEwen '431, wherein a velcro-type fastening patch facilitates releasable attachment of a cuff end to a mating velcro-type cuff surface as in Bellin '549 so that the overlapping bladder is secured in a substantially circumferential direction around the limb, and wherein a velcro-type fastening strap engages with a mating velcro-type surface of the cuff to secure the cuff around the limb.

To help secure the end of the cuff in contact with the limb and to aid in cuff alignment during application, a number of cuffs in the prior art include a tie strap attached near one end of the cuff. Typical cuffs which include a tie strap are described by McEwen et al. in U.S. Pat. No. 6,682,547 and by Robinette-Lehman in U.S. Pat. No. 4,635,635. A tie strap allows a surgical user to achieve a snug application of the cuff to the limb, and when tied helps assure that the overlapping portion of the cuff remains aligned, thus helping to prevent twisting, telescoping and rolling of the cuff when inflated, and thus helping to assure the most effective transmission of pressure from the cuff to the limb. Prior-art tourniquet cuffs include tie straps that are attached to cuffs in a variety of ways, including sewing or bonding to a surface of the cuff. It is not desirable to attach the tie strap to the cuff surface facing the patient's limb, where such attachment may distort the cuff surface and thus lead to uneven pressure distribution and possible soft-tissue injury. An alternate method of attaching the tie strap to the end of a cuff is shown in Goldstein et al. '518. Some prior art cuffs such as Spence '304 do not include a tie strap, but such cuffs are less conveniently applied, and may result in an applied cuff that is less snug and less effective in transmitting pressure from the cuff to the limb.

Some prior art cuffs carry marking visible to a surgical user, as described for example by McEwen in U.S. Pat. No. 4,605,010 and U.S. Pat. No. 5,312,431. Typical markings carried on tourniquet cuffs of the prior art have included labels sewn to cuff components and ink lettering and symbols marked on cuff surfaces. Some tourniquet cuffs of the prior art are marked by manufacturers to indicate that they are intended for single use only. Unauthorized reprocessing and reuse of such tourniquet cuffs in multiple surgical procedures may be hazardous for patients. However, such marking on prior-art cuffs may be easily removed or obscured if the cuffs are reprocessed, leading to the possibility that surgical staff may unknowingly use disposable tourniquet cuffs that have been reprocessed in a manner not authorized by the manufacturer and hazardous to patients.

In general, it is desirable to construct the thinnest tourniquet cuff possible for a given application. Thinner cuffs have smaller differences in circumference between inner cuff surfaces and outer cuff surfaces when encircling a patient's limb, in comparison to thicker cuffs. Such smaller differences in circumference reduce folding and wrinkling at the inner cuff surface. This reduces the possibility of wrinkling, pinching, bruising and other injuries to the skin and soft tissue encircled by such cuffs. Further, thinner cuffs tend to be less rigid than thicker cuffs and thus allow a surgical user to apply the cuff more snugly and more easily to the limb.

The manufacturing and assembly process of prior art cuffs consists of numerous cutting, sewing, and sealing operations which require substantial investment in both equipment and skilled operators. The manual labor component of cuff assembly is high, especially where multiple sewing and sealing operations are required. It is therefore desirable to reduce the skill and time required by the cuff assembly process, while continuing to utilize readily available manufacturing equipment. A reduction in the amount of time and skill required to manufacture tourniquet cuffs can be accomplished by reducing the number of manual assembly operations. This may include the elimination of numerous sewing operations, and the consolidation of multiple RF sealing steps into a single operation. Reducing the number of manual operations provides a savings not only in the labor to construct a cuff, but also provides the potential for the automation of a number of steps leading to the single cuff sealing operation.

In U.S. Pat. No. 6,682,547 McEwen et al. describe a method for automating the cuff manufacturing process by constructing the top layer of the cuff in a continuous strip having varying thickness to provide the stiffening functions described previously while not limiting the inward radial expansion of the bladder. McEwen '547 describes a custom manufacturing process which allows the bottom and top layers to be joined in a continuous process, whereby the edge of the inner layer is folded over the outer layer and sealed. The end edges of the cuff are sealed at various intervals to allow the construction of cuffs of a variety of lengths. The stiffened top layer therefore extends to the ends of the resulting cuff. Manufacturing the tourniquet cuff described in McEwen '547 requires a high level of investment in automated manufacturing equipment and processes, and necessarily requires a high volume of cuff manufacture to produce low-cost cuffs.

There is a need for a disposable tourniquet cuff which overcomes the hazards, problems and limitations of performance associated with prior-art cuffs as described above, and which can be manufactured at substantially lower cost with few changes to existing manufacturing equipment and processes.

BRIEF DESCRIPTION OF THE DRAWINGS

FIG. 2 is an exploded view of the preferred embodiment.

FIGS. 3a and 3b are top views of the preferred embodiment.

FIGS. 4a, 4b and 4c are section views taken from FIG. 3a.

FIG. 6 is a top view of the preferred embodiment showing a securing strip.

DETAILED DESCRIPTION OF THE PREFERRED EMBODIMENT

Figure 1:
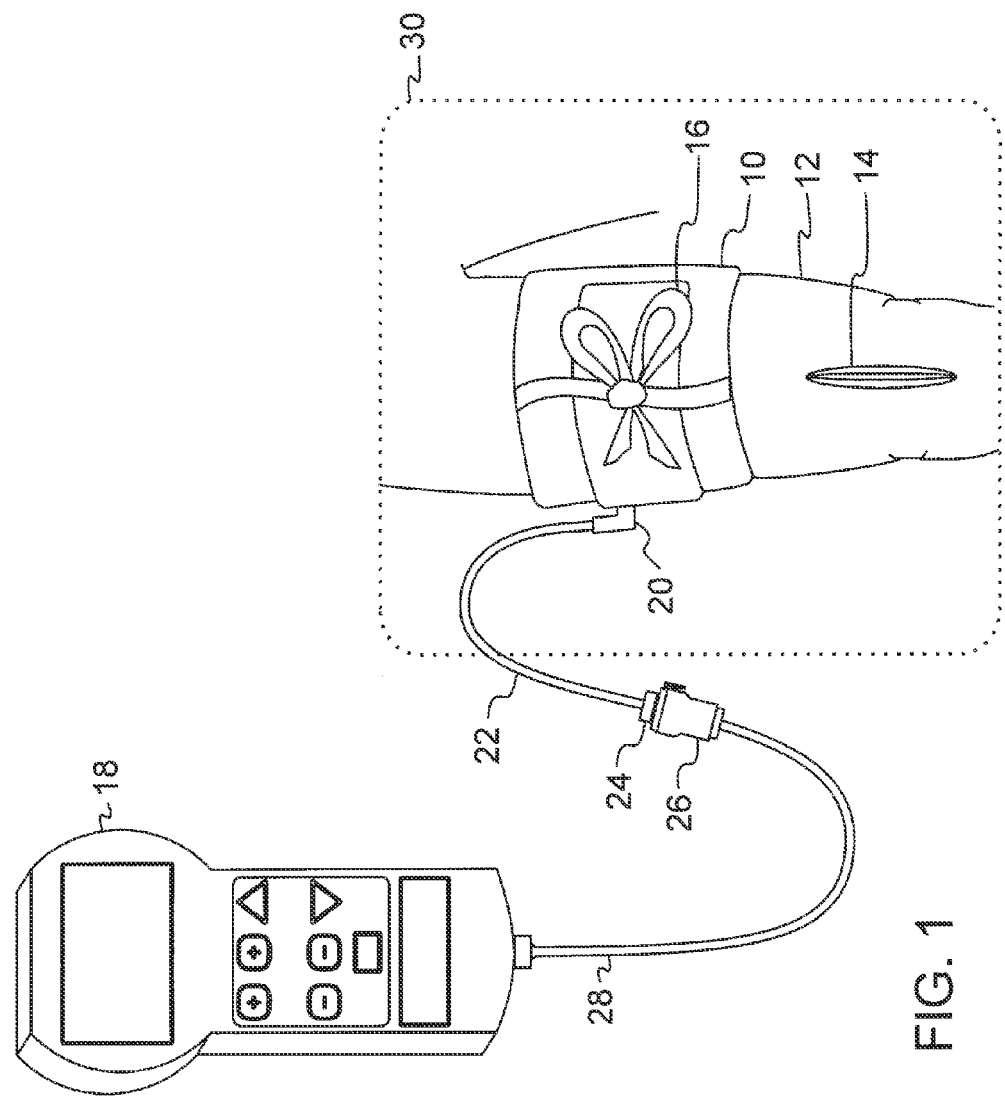
FIG. 1 is a pictorial representation of the preferred embodiment in a surgical application.

FIG. 1 is a pictorial representation of the preferred embodiment in a surgical application, showing tourniquet cuff 10 secured circumferentially around patient limb 12 proximal to surgical site 14. Tie strap 16 described further below, is tied as shown in FIG. 1 to help prevent the cuff 10 from sliding proximally or distally on patient limb 12 when cuff 10 is inflated.

The inflatable portion of tourniquet cuff 10 completely encircles patient limb 12 and is pneumatically connected to tourniquet instrument 18 via cuff port 20, cuff tubing 22, cuff connector 24, instrument connector 26 and instrument tubing 28. Tourniquet instrument 18 supplies pressurized gas for the inflation of cuff 10 and is capable of inflating cuff 10 to a pressure that will occlude the flow of arterial blood in patient limb 12 distal to cuff 10.

The perimeter of a sterile surgical field 30 encloses surgical site 14, a portion of patient limb 12, tourniquet cuff 10, and a portion of cuff tubing 22. Cuff tubing 22 is of sufficient length to permit cuff connector 24 to be releasably mated with instrument connector 26 outside of sterile surgical field 30. In the preferred embodiment shown, cuff 10 is a single port cuff, where cuff port 20 provides a single pneumatic passageway into the inflatable portion of cuff 10. Those skilled in the art will appreciate that the features described in the preferred embodiment may also be applied to tourniquet cuffs having more than one port, such as those described by U.S. Pat. No. 4,469,099, No. 4,479,494, and No. 5,254,087.

As described below, cuff 10 is constructed of materials that are appropriate for a single-use sterile disposable tourniquet cuff. To permit cuff 10 to be used in a sterile surgical field, cuff 10 is sterilized at time of manufacture by exposure to a sterilizing agent within a sterilizing process determined to be safe and effective. To prevent deterioration of the cuff, and to maintain the integrity of the pneumatic passageways within cuff 10, a sterilization agent and process that will not harm the materials or components of cuff 10 is selected by the manufacturer. In the preferred embodiment cuff 10 is sterilized by exposure to gamma radiation or electron beam radiation.

The cost of materials and labor are important considerations in the manufacture of tourniquet cuffs intended for a single use and then disposal. To minimize the cost of materials and assembly of cuff 10, materials are selected which are not intended to withstand exposure to subsequent sterilization and cleaning processes. The subsequent sterilization or cleaning of cuff 10 by agents and processes commonly used in health care facilities, such as ethylene oxide gas sterilization, hydrogen peroxide gas sterilization, high temperature and pressure steam sterilization, sterilization by other chemical agents, and pasteurization, are all capable of adversely affecting the integrity of the materials and pneumatic passageways of cuff 10.

Cuff 10 includes marking such as symbols or letters to indicate to that cuff 10 is intended for a single patient use and is to be discarded after use. Marking may also be present to identify the manufacturer of cuff 10 and indicate a manufacturing lot number.

The preferred embodiment includes marking to indicate that the cuff is intended for a single use and the marking is permanently formed in selected welded areas of cuff 10 as described further below. This permanent marking can be easily read by a user and cannot be easily obscured or removed from the cuff without causing damage to the cuff. Typical prior art cuffs include marking printed with ink onto labels which are then sewn onto the cuff or printed with ink directly onto the cuff, and marking printed onto the sterile packaging in which the cuff is provided to the user. Additionally, marking within bonded areas of a cuff is described by McEwen et al. in U.S. Pat. No. 6,682,547.

Printed cuff packaging can be easily lost or thrown away and sewn on labels can be inadvertently or intentionally removed from these prior art cuffs. Marking printed with ink directly on the cuff may be obscured, and ink fragments may come loose and contaminate the surgical field. If a cuff is not clearly marked as intended for single use a user or third party could unknowingly attempt to re-manufacture and re-sterilize the cuff contrary to the original manufacturer's instructions thereby producing a cuff that is possibly hazardous to patients.

FIG. 2 is an exploded view of the individual components that are joined together as described below to form cuff 10. For clarity, cuff tubing 22 and cuff connector 24 are not shown in FIG. 2.

Those skilled in the art will appreciate that many conventional methods exist for joining the thermoplastic polymers that comprise the materials of cuff 10. Joining processes can be separated into two broad groups: adhesive bonding, and thermal or solvent welding. In an adhesive bonding process, an adhesive layer is applied between two or more materials and when cured, the adhesive holds the materials together at their surfaces. In a thermal or solvent welding process, the surfaces of two or more materials are made fluid by applying either thermal heating or a solvent, which allow the thermoplastic materials to molecularly diffuse into one another forming a weld. For molecular diffusion to occur the thermoplastic polymers being thermally or solvent welded must be sufficiently compatible. Thermal or solvent welding will not occur between incompatible materials, for example, polyurethane and polyethylene. Thermal welding can be accomplished by numerous methods, including direct heating (e.g., hot gas, infrared, extrusion), induced heating (e.g., radio frequency (RF) or dielectric welding), and frictional heating (e.g., ultrasonic welding). In the preferred embodiment and as described below, the thermoplastic polymers comprising components of cuff 10 are joined together by the dielectric welding process, in which materials are brought together under pressure in a die and radio frequency energy is applied to temporarily melt a portion of the thermoplastic materials causing them to weld together in a selected area. Dielectric welding relies on the principle of dielectric heating to induce heat in thermoplastic materials placed within an alternating electromagnetic field. The amount of potential heating generated is dependent upon the dielectric properties of the thermoplastic materials, known as loss factor or dissipation factor. Thermoplastics with a relatively high dissipation factor such as polyurethane can be readily dielectrically welded, while thermoplastics with low dissipation factors such as polyethylene can not be readily welded by this process. While thermoplastic polyethylene will not heat substantially during the dielectric welding process it will still provide a conductive path through which the alternating electromagnetic field will propagate allowing welding to occur in adjacent materials.

Some materials that comprise components of cuff 10 are attached by stitches formed from nylon thread. It will be apparent that other types of mechanical fastening methods such as stapling and riveting could be used to attach selected components of cuff 10. Unlike joints formed by adhesive bonds and welds described above that can form gas-tight seals, materials that are sewn together or otherwise mechanically fastened generally do not form gas-tight seals between components.

To reduce manufacturing equipment and labor costs it is desirable to manufacture cuff 10 in a single dielectric welding operation. This requires that the thermoplastic polymers comprising the components of cuff 10 be prevented from welding at selected surfaces. Preventing thermoplastic materials from welding together can be accomplished by several methods. One method involves coating the surface of a thermoplastic material with a material that prevents the molecular diffusion into another otherwise compatible material. Another method involves selecting thermoplastic materials that have markedly different dissipation factors, preventing one or more of the materials from heating during a dielectric welding operation. As described above, both methods may be employed in the manufacture of cuff 10.

Referring to the components of cuff 10 shown in FIG. 2, securing strap 32 is made of a nylon hook material that is commonly used in hook and loop velcro-type fastening applications. Velcro-type fasteners form releasable connections between two mating surfaces. When the velcro-type surfaces are engaged they resist shear and tensile forces. The surfaces are typically released by peeling the surfaces apart from an edge. In use, securing strap 32 engages with loop material on the outer surface of top sheet 34. When cuff 10 is applied to a limb, securing strap 32 is engaged by a user to the loop material of top sheet 34 to secure cuff 10 circumferentially around the limb. The length and specifications of the hook material comprising securing strap 32 are selected to maintain cuff 10 securely around the limb circumference when cuff 10 is inflated.

Top sheet 34 is a thin flexible nylon loop material adapted for secure engagement with the hook material of securing strap 32. Top sheet 34 is coated on the inner surface with a thermoplastic polymer. This thermoplastic polymer coating prevents the passage of gas through top sheet 34 and allows top sheet 34 to be joined to cuff port 20, bottom sheet 36 and to stiffener 38 as described below. In the preferred embodiment the thermoplastic coating on top sheet 34 is polyurethane. It will be apparent that securing strap 32 could be comprised of a loop material and top sheet 34 could be a hook material. It will also be appreciated that other velcro-type materials, including adhesives that have velcro-type properties, could be selected to comprise securing strap 32 and top sheet 34.

Bottom sheet 36 is made of flexible woven cloth coated on the inner surface with a thermoplastic polymer. The thermoplastic polymer coating prevents the passage of gas through bottom sheet 36 and allows bottom sheet 36 to be joined to top sheet 34 as described above and below. In the preferred embodiment the thermoplastic coating on bottom sheet 36 is polyurethane. It will be appreciated by those skilled in the art that other thermoplastic polymers, polyvinylchloride for example, may be used as coatings on top sheet 34 and bottom sheet 36 providing they can be joined with sufficient strength to maintain the integrity of cuff 10 when inflated.

As shown in FIG. 2, cuff port 20 has a right angle configuration and includes a flange. Cuff port 20 is made of a thermoplastic polymer that is compatible with and can be joined to the thermoplastic coating of top sheet 34 to form a gas-tight seal.

Tie strap 16 is a soft fabric ribbon material that is shown in FIG. 2 positioned between bottom sheet 36 and top sheet 34. As described below, tie strap 16 is secured to the inner coated surface of bottom sheet 36. This configuration positions the tie strap 16 away from the surface of the patient limb and promotes even pressure distribution from the overlapping bladder. Tie strap 16 may also be secured to the inner surface of top sheet 34. Tie strap 16 provides a means for the user to align and pull cuff 10 snug around the limb when tied as shown in FIG. 1, helps maintain the overlapping portion of the cuff in alignment around the limb by preventing the inflated cuff from twisting, telescoping and rolling on the limb when inflated. Tie strap 16 may be coated with a thermoplastic polymer that is compatible with the polymer coating on bottom sheet 36 to permit it to be welded to bottom sheet 36 or may be comprised of materials that adhere to the coated surfaces of bottom sheet 36 and top sheet 34.

Secondary fastener 40 is hook material similar to the hook material that comprises securing strap 32. Secondary fastener 40 is attached to the outer surface of bottom sheet 36 and engages with the loop material of top sheet 34. Secondary fastener 40 facilitates cuff application and alignment of the cuff by providing a means for maintaining cuff 10 in position around patient limb 12 while securing strap 32 is engaged. Secondary fastener 40 acts independently of securing strap 32 providing increased safety by helping to ensure the cuff remains overlapped and secured in a substantially circumferential direction if securing strap 32 is not engaged or becomes ineffective while the cuff is inflated.

Stiffener 38 is made of a gas impermeable thermoplastic polymer sheet cut to a rectangular shape to fit within the perimeter of bladder perimeter weld 42 shown in FIGS. 3a, 3b and 6. The length dimension of stiffener 38 is at least equal to the circumference of patient limb 12 at the location that cuff 10 is applied to patient limb 12. Top sheet 34 and bottom sheet 36 are welded together at bladder perimeter weld 42 to form an inflatable bladder 44 shown in FIGS. 4a, 4b, 4c, and 5. The length dimension of inflatable bladder 44 is greater than the circumference of patient limb 12 at the location that cuff 10 is applied to patient limb 12.

Stiffener 38 is less flexible than top sheet 34 and bottom sheet 36 but is flexible enough to be wrapped around a limb (for example, 0.020" thick polyurethane/polyvinylchloride alloy sheet or polyethylene sheet). The properties of stiffener 38 are selected such that the forces required to bend stiffener 38 across its width are significantly greater than those required to bend top sheet 34 across its width by an equal amount. When secured circumferentially around the limb as shown in FIG. 1, stiffener 38 helps direct the expansion of inflatable bladder 44 radially inwards towards the limb upon inflation of cuff 10. The stiffener thus provides uniformly distributed pressure onto limb. Attaching stiffener 38 to top sheet 34 prevents top sheet 34 from moving relative to stiffener 38 and thereby helps prevent cuff 10 from rolling down patient limb 12 when cuff 10 is inflated. The attachment of stiffener 38 to top sheet 34 permits the use of thin flexible materials for top sheet 34 and bottom sheet 36 making for a thinner overall cuff which is desirable as thin cuffs afford an improved fit to the patient limb with less wrinkling of materials. Some prior art cuffs with a stiffener floating within the bladder use heavier stiffer materials for the bladder walls to resist rolling along the limb. These thick materials result in increased wrinkling of the bladder surfaces when the cuff is applied to the limb.

The width of stiffener 38 is less than the width of inflatable bladder 44 when cuff 10 is laid flat. The width of stiffener 38 determines the degree to which bladder 44 can expand (or reach) to apply pressure into the limb. Unlike prior art cuffs that have a stiffener extending beyond the width of the inflatable bladder, cuff 10 has greater reach and thereby results in lower limb occlusion pressures than those obtainable with prior art cuffs. In the preferred embodiment a surface of the thermoplastic polymer that comprises stiffener 38 is compatible with the thermoplastic coating of top sheet 34 and is welded to the inner surface of top sheet 34 by the dielectric welding process described above. Stiffener 38 is prevented from welding to the inner surface of bottom sheet 36 by an incompatible coating which is applied as described below to either a surface of stiffener 38 or to a portion of the inner surface of bottom sheet 36.

Welds that attach the inner surface of top sheet 34 to stiffener 38 form gas-tight seals at their perimeters and define a non-inflatable portion or portions of top sheet 34. In prior art cuffs with floating or unattached stiffeners within the bladder the outer surface of the bladder is free to expand outward away from the limb when the cuff is inflated. This expansion or "ballooning" of the outer surface of the bladder is undesirable, especially in areas where velcro-type fasteners are mated to the outer surface to secure the cuff around the limb. In the preferred embodiment non-inflatable portions of top sheet 34 and stiffener 38 remain in substantially the same plane and do not balloon outward when the cuff is inflated thus providing a more secure attachment area for velcro-type fasteners.

FIGS. 3a and 3b are top views of the preferred embodiment laid flat showing the areas where the inner surface of top sheet 34 are welded to bottom sheet 36, cuff port 20 and stiffener 38. The separate weld areas shown in FIGS. 3a and 3b are: bladder perimeter weld 42, cuff port weld 46, tie strap retaining weld 48, and stiffener retaining weld 52. The dies used to form these welds may be adapted to produce marking in bladder perimeter weld 42 and stiffener retaining weld 52. The marking that is formed is integral to the welded areas and easily visible to a user as described above to indicate to a user that cuff 10 is intended for a single use only. Bladder perimeter weld 42 defines inflatable bladder 44 of cuff 10 which is shown in FIGS. 4a, 4b, 4c, and 5. Cuff port 20, cuff tubing 22 and cuff connector 24 provide a pneumatic passageway communicating with inflatable bladder 44 through which bladder 44 may be inflated.

The perimeters of stiffener retaining weld 52 and cuff port weld 46 define a non-inflatable portion of top sheet 34. This non-inflatable portion of top sheet 34 does not form part of inflatable bladder 44 and pressurized gas does not contact this portion of top sheet 34.

FIG. 3a shows non-inflating region weld 50, the perimeter of which defines a non-inflating region near the end edge of cuff 10. In FIG. 3a, securing strap 32 is shown sewn at location 54 to the upper surface of cuff 10 (outer surface of top sheet 34) within the perimeter of non-inflating region weld 50, in the preferred embodiment secondary fastener 40 is also sewn to the bottom surface of cuff 10 (outer surface of bottom sheet 36) at location 54 opposite the attachment point of securing strap 32. It will be apparent that securing strap 32 and secondary fastener 40 may be attached by other mechanical fastening means or by welding or adhesives. It will also be apparent that a surface of securing strap 32 may be coated with a thermoplastic polymer and joined by welding in between top sheet 34 and bottom sheet 36.

In FIG. 3*b* bladder perimeter weld 42 is shown extended to near the end edge of cuff 10 eliminating non-inflating region weld 50. It will be apparent that the width of the bladder perimeter weld 42 may be increased near the end edge of the cuff to join top sheet 34 to bottom sheet 36 out to the end edge of cuff 10.

In FIG. 3*b* securing strap 32 is shown non-releasably attached to the non-inflatable portion of top sheet 34 within the perimeter of stiffener retaining weld 52 at location 56. Securing strap 32 may be sewn or attached by other mechanical fastening means to top sheet 34 as the attachment is not required to be gas-tight as it is made within the non-inflatable portion of top sheet 34. Securing strap 32 may also be welded or adhesively bonded at location 56 to non-releasably attach securing strap 32 to top sheet 34.

The length of securing strap 32 may also be increased to permit a greater area of engagement of the hook and loop materials of securing strap 32 and top sheet 34 within the non-inflatable portion of top sheet 34. If the area of hook and loop engagement is sufficiently large to maintain cuff 10 secured around a limb when inflated, the attachment at location 56 may be eliminated.

When cuff 10 is secured around a limb and inflated, securing strap 32 comes under considerable tension. The amount of tension securing strap 32 and its attachment location is subject to and dependent upon the circumference of the limb and the pressure to which bladder 44 is inflated. In the configuration of cuff 10 shown in FIG. 3*b* securing strap 32 includes a hole formed to allow cuff port 20 to pass through securing strap 32. When securing strap 32 comes under tension securing strap 32 may stretch and move slightly. In the preferred embodiment the hole formed in securing strap 32 is sized, shaped, and positioned to prevent securing strap 32 from transferring load to the sides of cuff port 20 when securing strap 32 is tensioned.

Figure 5:
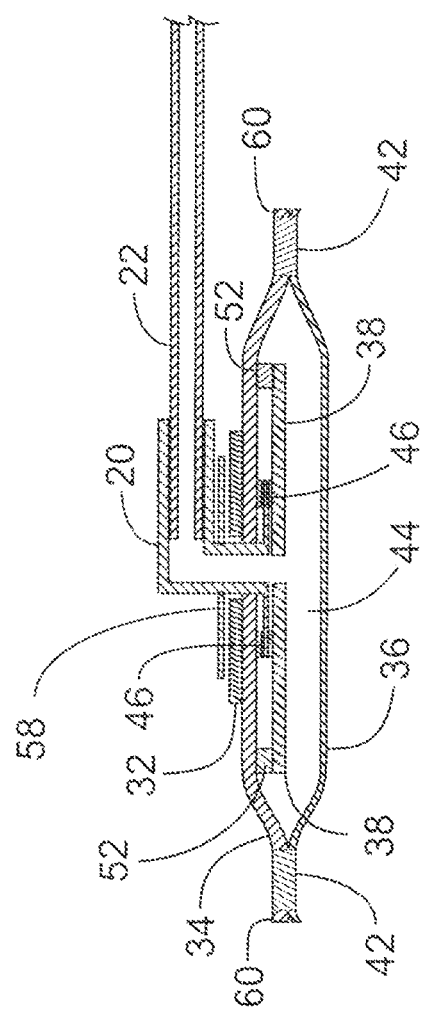
FIG. 5 is a section view taken from FIG. 3b.

As shown in FIG. 3*b* and shown in cross section in FIG. 5 securing strap 32 is also non-releasably attached to cuff 10 by retaining ring 58. Retaining ring 58 is formed from rigid thermoplastic and non-releasably engages within a grove formed in cuff port 20. Retaining ring 58 has an outer diameter that is greater than the diameter of the hole that is formed in securing strap 32 for cuff port 20 to pass through. Retaining ring 58 acts to prevent detachment of securing strap 32 by a surgical user from top sheet 34 near the location of cuff port 20.

The attachment of securing strap 32 within the non-inflatable portion of top sheet 34 allows loads to be transferred from securing strap 32 to stiffener 38 by stiffener retaining weld 52. Top sheet 34 may be joined to stiffener 38 in additional locations to aid in the transfer of loads from securing strap 32 to stiffener 38.

When cuff 10 is configured as shown in FIG. 3*b*, secondary fastener 40 may be attached to the outer surface of bottom sheet 36 by welding or by an adhesive.

Tie strap 16 is permanently attached to cuff 10 by tie strap retaining weld 48 shown in FIGS. 3*a*, 3*b*, and 6. Top sheet 34, tie strap 16, and bottom sheet 36 are joined together at tie strap retaining weld 48.

Figure 4A:
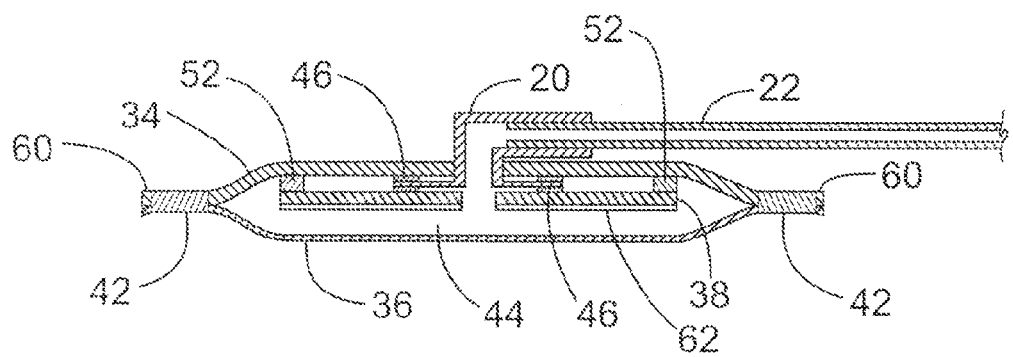
Figure 4B:
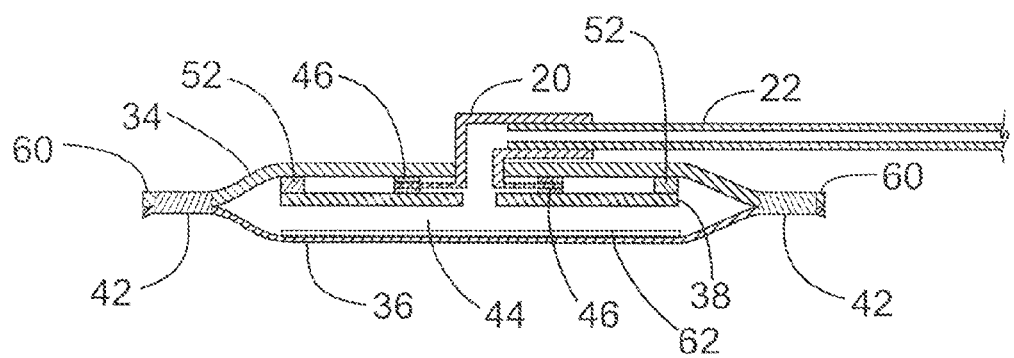
Figure 4C:
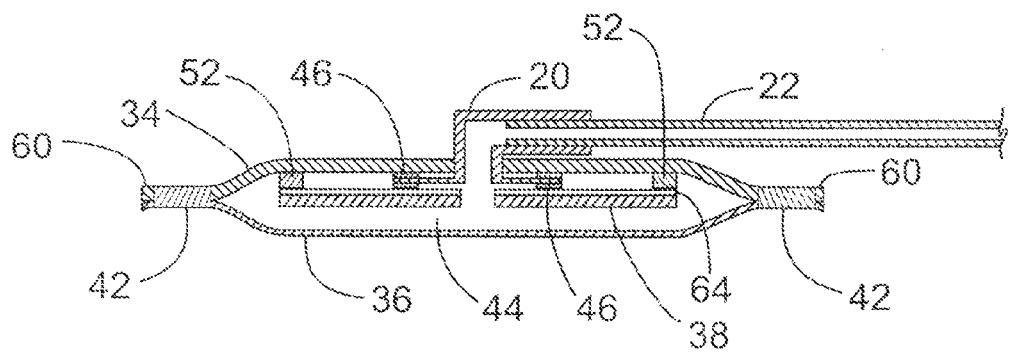

Cross section 4 from FIG. 3*a* of cuff 10 is shown in FIGS. 4*a*, 4*b* and 4*c*. FIGS. 4*a*, 4*b* and 4*c* depict the regions where surfaces of the components of cuff 10 are joined together by welds and show alternate methods for preventing selected surfaces of the components of cuff 10 from forming welds during the welding process.

Referring to FIG. 4*a*, top sheet 34 is joined to bottom sheet 36 at bladder perimeter weld 42 forming inflatable bladder 44. In the preferred embodiment bladder perimeter weld 42 does not extend to the longitudinal side edges of top sheet 34 and bottom sheet 36 thereby leaving a non-welded edge 60 along the length of cuff 10. This non-welded edge provides a softer more compliant edge for patient comfort than can be obtained when the width of the bladder perimeter weld 42 extends completely to the side edges of top sheet 34 and bottom sheet 36.

Cuff port 20 is joined to the inner surface of top sheet 34 and outer surface of stiffener 38 at the location of cuff port weld 46.

As shown in FIGS. 3*a* and 3*b*, stiffener retaining weld 52 is formed around the perimeter of stiffener 38 and acts to non-releasably attach the outer surface of stiffener 38 to the inner surface of top sheet 34, thereby preventing stiffener 38 from moving relative to top sheet 34 when cuff 10 is inflated. As described above, the perimeter of stiffener retaining weld 52 defines a non-inflatable portion of top sheet 34. Stiffener retaining weld 52 is shown in FIGS. 3*a* and 3*b* as a contiguous weld defining a single non-inflatable portion of top sheet 34, it will be apparent that top sheet 34 could be joined to stiffener 38 by multiple welds forming multiple non-inflatable portions of top sheet 34.

As shown in FIG. 4*a* the thermoplastic polymer of stiffener 38 is compatible with the thermoplastic coating on the inner surface of top sheet 34 and the two surfaces can be welded to each another. To permit cuff 10 to be manufactured in a single dielectric welding operation, a barrier 62 is applied to the inner surface of stiffener 38. Barrier 62 is a coating of thermoplastic material (for example polyethylene) that is not compatible with the thermoplastic coating on the inner surface of bottom sheet 36 and acts to prevent stiffener 38 from welding to the thermoplastic coating on the inner surface of bottom sheet 36 at the location of stiffener retaining weld 52 and cuff port weld 46.

The cross section of cuff 10 shown in FIG. 4*b* illustrates an alternate location for barrier 62. As shown in FIG. 4*b* barrier 62 is applied to a region of the inner surface of bottom sheet 36 such that stiffener 38 is prevented from welding with the thermoplastic coating on the inner surface of bottom sheet 36 at the location of stiffener retaining weld 52 and cuff port weld 46.

In FIG. 4*c*, stiffener 38 is formed from a thermoplastic which will not weld with the thermoplastic coatings on top sheet 34 and bottom sheet 36, such as polyethylene. To permit a stiffener made of an incompatible thermoplastic to be attached to the inner surface of top sheet 34, a stiffener coating 64 of a compatible thermoplastic such as polyurethane is laminated to the outer surface of stiffener 38. This laminated coating allows stiffener 38 to be non-releasably attached to the inner surface of top sheet 34. It will also be appreciated that stiffener 38 may be non-releasably attached to the inner surface of top sheet 34 by an adhesive bond by selecting and applying an adhesive compatible with the thermoplastic surfaces of top sheet 34 and stiffener 38.

To reduce material costs cuff 10 may be configured as shown in FIG. 6. In FIG. 6 cuff 10 is shown with a securing strip 66 joined to the outer surface of top sheet 34. Securing strip 66 is a strip of nylon loop material compatible with the hook material of securing strap 32. Securing strip 66 is coated on one surface with thermoplastic polymer material. In FIG. 6 top sheet 34 is configured as woven nylon fabric with a thermoplastic polymer coating on both the inner and outer surfaces. The thermoplastic polymer coating on the outer surface is typically thinner than the coating on the inner surface and provides a weldable surface for the attachment of securing strip 66. As shown in FIG. 6, securing strip 66 is attached to top sheet 34 at securing strip perimeter weld 68. Securing strip 66 is also attached to top sheet 34 by cuff marking weld 70. The shape of cuff marking weld 70 is selected to form the standard symbol for single use only devices to indicate to a user that cuff 10 is intended for a single use only. Stiffener 38 may also be bonded to the inner surface of top sheet 34 at the locations of securing strip perimeter weld 68 and cuff marking weld 70 to form non-inflatable portions of top sheet 34.

A portion of securing strap 32 is non-releasably attached to securing strip 66 at location 72. Securing strap 32 may be attached to securing strip 66 by sewing or welding. The length of securing strap 32 may also be increased to permit a greater area of engagement of the hook and loop materials of securing strap 32 and securing strip 66. If the area of hook and loop engagement is sufficiently large to maintain cuff 10 secured around a limb when inflated, the attachment at location 72 may be eliminated.

A hole formed in securing strap 32 as described above allows cuff port 20 to pass through securing strap 32. As shown in FIG. 6 securing strap 32 is also attached to cuff 10 at location 74 beyond the end edge of bladder perimeter weld 42. In the preferred embodiment securing strap 32 is attached at location 74 by sewing through top sheet 34 and bottom sheet 36. The attachment of securing strap 32 at location 74 allows loads from securing strap 32 to be distributed to bottom sheet 36 and evenly to both sides of cuff port 20, it also prevents a user from applying loads to cuff port 20 when manipulating securing strap 32 during cuff application and removal. If securing strap 32 is not non-releasably attached at location 72, the non-releasable attachment at location 74 acts to maintain securing strap 32 in the correct position and orientation on cuff 10 and prevents securing strap 32 from being inadvertently removed from cuff 10 by a user. Securing strap 32 may also be attached at location 74 by other mechanical fastening methods or by adhesives or welding. Top sheet 34 and bottom sheet 36 may be welded together at location 74 to provide a stronger area for the attachment of securing strap 32.

The embodiment illustrated is not intended to be exhaustive or limit the invention to the precise form disclosed. It is chosen and described in order to explain the principles of the invention and its application and practical use, and thereby enable others skilled in the art to utilize the invention.

The invention claimed is:

1. A low-cost tourniquet cuff apparatus for encircling a patient's limb at a desired location on the limb, comprising:
   a first sheet formed of gas-impermeable flexible material that includes a first thermoplastic polymer;
   a second sheet formed of gas-impermeable material that is positioned facing the first sheet and that includes a second thermoplastic polymer;
   a gas-tight peripheral seal joining the first sheet directly to the second sheet around a perimeter of those sheets to form an inflatable bladder within the perimeter, wherein the bladder has a length;
   a securing strap attached to the cuff apparatus and adapted to allow surgical staff to encircle the cuff apparatus around the limb at a desired location on the limb so that the bladder overlaps upon itself;
   a stiffener fitting inside the bladder and sized to extend substantially the length of the bladder but not the entire bladder length, and to fit completely within the peripheral seal, the stiffener including a stiffener surface facing the first sheet and formed of a material that includes a thermoplastic polymer, wherein the polymers of the stiffener surface and the first sheet are selected to have physical properties that facilitate welding together;
   wherein the stiffener surface is separate from the second sheet and the stiffener surface is welded to the first sheet at a location within the bladder and away from the peripheral seal;
   a tubular port connected to the bladder for directing gas into the bladder from a tourniquet instrument to which the port may be releasably connected; and
   a cuff marking weld located on an outer surface of the cuff apparatus away from the gas-tight peripheral seal wherein the cuff marking weld has a shape selected to form a symbol visible to a user.

2. Low-cost tourniquet cuff apparatus for encircling a patient's limb at a desired location on the limb, comprising:
   a first sheet formed of flexible material that is impermeable to gas and that includes a first thermoplastic polymer;
   a second sheet formed of flexible material that is impermeable to gas and that is positioned facing the first sheet and that includes a second thermoplastic polymer;
   a gas-tight seal joining the first sheet directly to the second sheet around a perimeter to form an inflatable bladder within the perimeter, wherein the inflatable bladder has a width and a length;
   a securing strap attached to the cuff apparatus and adapted to allow surgical staff to encircle the cuff apparatus around the limb at a desired location on the limb so that the bladder overlaps upon itself;
   a port communicating with the bladder and releasably connectable to a tourniquet instrument for establishing a pneumatic passageway for pressurized gas between the bladder and the connected tourniquet instrument;
   a stiffener formed of material that is less flexible than the first sheet, wherein the stiffener has a width that is less than the bladder width and a length defined between opposing ends thereof, the stiffener length extending substantially the length of the bladder but less than the bladder length, wherein the stiffener includes a first stiffener surface facing the first sheet and formed of a material that includes a thermoplastic stiffener polymer, wherein the polymers of the first stiffener surface and the first sheet have physical properties that facilitate welding together, and wherein the stiffener surface is welded to the first sheet at a location within the bladder and away from the gas-tight seal around the perimeter; and
   a cuff marking weld located on an outer surface of the cuff wherein the marking weld has a shape selected to form a symbol visible to a user.

3. A method of making a low-cost tourniquet cuff for encircling a patient's limb, comprising the steps of:
   providing a first sheet formed of gas-impermeable flexible material that includes a first thermoplastic polymer;
   providing a second sheet formed of gas-impermeable material that is positioned facing the first sheet and that includes a second thermoplastic polymer;
   joining the first sheet directly to the second sheet with a gas-tight peripheral seal around a perimeter of those sheets, thereby to form an inflatable bladder within the perimeter, wherein the bladder has a length;
   configuring the bladder to have a length sufficient for overlapping upon itself when encircled around the limb;

fitting inside the bladder a stiffener having a stiffener surface that is formed of a material that includes a thermoplastic polymer, the stiffener being sized to extend substantially the length of the bladder but not the entire bladder length, and to fit completely within the peripheral seal, selecting the polymers of the stiffener surface and the first sheet to have physical properties that facilitate welding together;

welding together part of the stiffener surface and the first sheet at a location within the bladder and away from the peripheral seal; and attaching to the inflatable bladder a tubular port for directing gas into the bladder from a tourniquet instrument to which the port may be releasably connected, the port defining a passageway therethrough; and marking an outer surface of the cuff apparatus by welding into the outer surface a shape forming a symbol visible to a user.

* * * * *